(12) United States Patent
Blinn et al.

(10) Patent No.: US 8,187,662 B2
(45) Date of Patent: *May 29, 2012

(54) METHOD OF CONTROLLING A DRUG RELEASE RATE

(75) Inventors: Stephen M. Blinn, Amherst, NH (US); Barry M. Zide, Medway, MA (US)

(73) Assignee: Exogenesis Corporation, Billerica, MA (US)

( * ) Notice: Subject to any disclaimer, the term of this patent is extended or adjusted under 35 U.S.C. 154(b) by 35 days.

This patent is subject to a terminal disclaimer.

(21) Appl. No.: 12/643,047

(22) Filed: Dec. 21, 2009

(65) Prior Publication Data

US 2010/0098833 A1    Apr. 22, 2010

Related U.S. Application Data

(60) Division of application No. 11/349,483, filed on Feb. 7, 2006, now Pat. No. 7,666,462, which is a continuation-in-part of application No. 10/144,919, filed on May 13, 2002, now Pat. No. 7,105,199.

(60) Provisional application No. 60/317,652, filed on Sep. 6, 2001, provisional application No. 60/290,389, filed on May 11, 2001.

(51) Int. Cl.
    *B05D 3/00*    (2006.01)
    *C23C 14/00*   (2006.01)

(52) U.S. Cl. ...... 427/2.24; 427/2.25; 427/523; 427/533; 427/534; 623/1.12; 424/422; 424/426

(58) Field of Classification Search ............... 427/2.24, 427/2.25, 523, 533, 534; 623/1.12; 424/422, 424/426

See application file for complete search history.

(56) References Cited

U.S. PATENT DOCUMENTS

| | | | |
|---|---|---|---|
| 3,710,795 A | 1/1973 | Higuchi et al. | |
| 4,986,006 A | 1/1991 | Weaver | |
| 5,123,924 A | 6/1992 | Sioshansi et al. | |
| 5,133,757 A | 7/1992 | Sioshansi et al. | |
| 5,419,760 A | 5/1995 | Narciso | |
| 5,459,326 A | 10/1995 | Yamada | |
| 5,763,504 A | 6/1998 | Matsuda et al. | |
| 5,814,194 A | 9/1998 | Deguchi et al. | |
| 5,843,172 A | 12/1998 | Yan | |
| 6,143,354 A | 11/2000 | Koulik et al. | |
| 6,207,282 B1 | 3/2001 | Deguchi et al. | |
| 6,331,227 B1 | 12/2001 | Dykstra et al. | |
| 6,451,871 B1 | 9/2002 | Winterton et al. | |
| 6,486,478 B1 * | 11/2002 | Libby et al. | 250/492.1 |
| 6,491,800 B2 | 12/2002 | Kirkpatrick et al. | |
| 6,641,607 B1 | 11/2003 | Hossainy et al. | |
| 6,676,989 B2 * | 1/2004 | Kirkpatrick et al. | 427/2.28 |
| 6,746,773 B2 | 6/2004 | Llanos et al. | |
| 6,764,505 B1 | 7/2004 | Hossainy et al. | |
| 6,863,786 B2 * | 3/2005 | Blinn et al. | 204/192.34 |
| 6,984,404 B1 | 1/2006 | Talton et al. | |
| 7,105,199 B2 * | 9/2006 | Blinn et al. | 427/2.24 |
| 7,666,462 B2 * | 2/2010 | Blinn et al. | 427/2.24 |
| 7,923,055 B2 * | 4/2011 | Blinn et al. | 427/2.24 |
| 7,931,683 B2 * | 4/2011 | Weber et al. | 623/1.42 |
| 2002/0017454 A1 | 2/2002 | Kirkpatrick | |
| 2002/0139961 A1 | 10/2002 | Kinoshita et al. | |
| 2002/0188324 A1 | 12/2002 | Blinn et al. | |
| 2003/0143315 A1 | 7/2003 | Pui et al. | |
| 2005/0025804 A1 * | 2/2005 | Heller | 424/423 |
| 2005/0043787 A1 | 2/2005 | Kutryk et al. | |
| 2005/0244453 A1 | 11/2005 | Stucke et al. | |
| 2007/0087034 A1 | 4/2007 | Blinn et al. | |
| 2008/0069858 A1 * | 3/2008 | Weber | 424/426 |
| 2009/0036373 A1 | 2/2009 | Lang | |
| 2009/0098186 A1 | 4/2009 | Kirkpatrick et al. | |
| 2010/0233227 A1 * | 9/2010 | Weber | 424/422 |

FOREIGN PATENT DOCUMENTS

| | | |
|---|---|---|
| JP | 1066721 A | 3/1998 |
| WO | 2009036373 A2 | 3/2009 |

OTHER PUBLICATIONS

PCT/US07/61787; Filed Feb. 7, 2007; Notification of Transmittal of International Search Report and the Written Opinion; Mailed Apr. 24, 2008.

Fehsenfeld P. et al., Production of Radioactive Stents:, Nachrichten Forschungszentrum Karlsruhe, 2000, pp. 81-86, vol. 32-1, Germany.

PCT/US07/61787; Filed Feb. 7, 2007; Notification Concerning Transmittal of International Preliminary Report on Patentability; mailed Aug. 21, 2008.

Matsuo, J. et al. "What size of cluster is most appropriate for SIMS?" Applied Surface Science 255 (2008) pp. 1235-1238.

* cited by examiner

*Primary Examiner* — Bret Chen

(74) *Attorney, Agent, or Firm* — Burns & Levinson LLP; Jerry Cohen; David W. Gomes

(57) ABSTRACT

A method of controlling the drug release rate of a drug coated endovascular stent by depositing a drug material layer on the stent and then modifying the drug material using gas cluster ion beam irradiation to create a carbon matrix with interstices containing the original drug. The rate at which the drug elutes through the interstices can be controlled by processing parameters. Multiple layers may be employed to create time varying release rates.

20 Claims, 12 Drawing Sheets

METHOD OF CONTROLLING A DRUG RELEASE RATE

CROSS-REFERENCE TO RELATED APPLICATIONS

This application is a division of U.S. patent application Ser. No. 11/349,483 filed Feb. 7, 2006 and entitled METHOD OF CONTROLLING A DRUG RELEASE RATE, now U.S. Pat. No. 7,666,462, which in turn is a continuation-in-part application of U.S. patent application Ser. No. 10/144,919 filed May 13, 2002, now U.S. Pat. No. 7,105,199 and entitled METHOD AND SYSTEM FOR IMPROVING THE EFFECTIVENESS OF MEDICAL DEVICES BY ADHERING DRUGS TO THE SURFACE THEREOF, which in turn claims the benefit of U.S. Provisional Application Ser. Nos. 60/290,389 filed May 11, 2001, and 60/317,652 filed Sep. 6, 2001, each entitled METHOD AND SYSTEM FOR IMPROVING THE EFFECTIVENESS OF MEDICAL DEVICES BY APPLYING/ADHERING DRUGS TO THEIR SURFACE IN COMBINATION WITH THE APPLICATION OF ION BEAM TECHNOLOGY, all applications being incorporated herein by reference in their entirety for all purposes.

FIELD OF THE INVENTION

This invention relates generally to drug delivery systems such as, for example, medical devices implantable in a mammal (e.g., coronary stents, prostheses, etc.), and more specifically to a method and system for applying and adhering drugs to the surface of medical devices using gas cluster ion beam technology in a manner that permits efficacious release of the drugs from the surface over time.

BACKGROUND OF THE INVENTION

A coronary stent is an implantable medical device that is used in combination with balloon angioplasty. Balloon angioplasty is a procedure used to treat coronary atherosclerosis. Balloon angioplasty compresses built-up plaque against the walls of the blocked artery by the inflation of a balloon at the tip of a catheter inserted into the artery during the angioplasty procedure. Unfortunately, the body's response to this procedure often includes thrombosis or blood clotting and the formation of scar tissue or other trauma-induced tissue reactions at the treatment site. Statistics show that restenosis or renarrowing of the artery by scar tissue after balloon angioplasty occurs in up to 35 percent of the treated patients within only six months after these procedures, leading to severe complications in many patients.

To reduce restenosis, cardiologists are now often placing a small metal tubular devices of various forms, such as wire mesh or expandable metal, called a coronary stent at the site of blockage during balloon angioplasty. The goal is to have the stent act as a scaffold to keep the coronary artery open after the removal of the balloon.

However, there are also serious complications associated with the use of coronary stents. Coronary restenotic complications associated with stents occur in 16 to 22 percent of all cases within six months after insertion of the stent and are believed to be caused by many factors acting alone or in combination. These complications could be reduced by several type of drugs introduced locally at the site of stent implantation. Because of the substantial financial costs associated with treating the complications of restenosis, such as catheterization, restenting, intensive care, etc., a reduction in restenosis rates would save money and reduce patient suffering.

Numerous studies suggest that the current popular designs of coronary stents are functionally equivalent. Although the use of coronary stents is growing, the benefits of their use remain controversial in certain clinical situations or indications due to their potential complications. It is widely held that during the process of expanding the stent, damage occurs to the endothelial lining of the blood vessel triggering a healing response that re-occludes the artery. To help combat that phenomenon, drug-coated stents are being introduced to the market to help control the abnormal cell growth associated with this healing response. These drugs are typically mixed with a liquid polymer and applied to the stent surface. When implanted, the drug elutes out of the polymer in time, releasing the medicine into the surrounding tissue. There remain a number of problems associated with this technology. Because the stent is expanded at the diseased site, the polymeric material has a tendency to crack and sometimes delaminate from the stent surface. These polymer flakes can travel throughout the cardio-vascular system and cause significant damage. There is some evidence to suggest that the polymers themselves cause a toxic reaction in the body. Additionally, because of the thickness of the coating necessary to carry the required amount of medicine, the stents can become somewhat rigid making expansion difficult. In other prior art stents, the wire mesh of the stent itself is impregnated with one or more drugs through processes such as high pressure loading, spraying, and dipping. However, loading, spraying and dipping do not satisfactorily adhere the drug to the stent surface and therefore, in many instances, do not yield the optimal, time-release dosage of the drugs delivered to the surrounding tissue.

It is therefore an object of this invention to provide a means of applying and adhering drugs to medical devices using gas cluster ion beam technology.

It is a further object of this invention to apply drugs to medical stents by gas cluster ion beams to decrease the complication of restenosis and thrombosis.

It is a further object of this invention to transform the surfaces of medical devices into drug delivery systems by applying and adhering drugs to the surfaces with gas cluster ion beams so as to facilitate a timed release of the drug(s) from the surfaces.

SUMMARY OF THE INVENTION

The objects set forth above as well as further and other objects and advantages of the present invention are achieved by the invention described hereinbelow.

The present invention is directed to the use of gas cluster ion-beam (GCIB) surface modification to implant, apply, or adhere various drug molecules directly into or onto the surface of a stent or other medical device, thereby eliminating the need for a polymer or any other binding agent and transforming the medical device surface into a drug delivery system. This will prevent the problem of toxicity and the damage caused by transportation of delaminated polymeric material throughout the body. Unlike the prior art stents described above that load the stent material itself, the present invention provides the ability to adhere for time-release an optimal dosage of the drug or drugs.

The application of the drug(s) is achieved through the use of GCIB technology. The application of the drug(s) is accomplished by several methods:

The surface of the medical device, which may be composed, for example, of a polymer, metal or any other material, is optionally first processed using a GCIB which will remove any contaminants and oxide layers from the surface rendering the surface electrically active and creating dangling bonds. The desired drug will then be deposited upon the active surface and will bond with the dangling bonds.

A second method for producing a drug delivery system involves depositing a layer of one or more drug substances onto at least one surface region of a medical device (which may or may not have been pre-processed with a GCIB) in liquid, powder or other form, perhaps through sublimating the drug, and then impacting the deposited drug layer with an energetic GCIB so as to form an adhered drug layer. The GCIB dose creates a carbonized drug matrix including a plurality of interstices through which non-carbonized drug will diffuse or elute over time. If the deposited drug layer is suitably thin, some GCIB clusters may penetrate through the deposited drug layer and reach the surface of the medical device, such that the adhered drug layer may include some portion of the deposited drug molecules implanted sub-surface in the form of a mechanical bond. If the deposited drug layer has a thickness above a threshold thickness (for a particular GCIB dose), however, the carbonized drug matrix will not be "stitched" to the surface of the medical device. Rather, the carbonized matrix will be formed over the remaining non-carbonized, mobile volume of the deposited drug. In one stent embodiment, for example, a ring-like, carbonized drug matrix is formed concentrically about a layer of non-carbonized, deposited drug which, in turn, is disposed about the stent on the stent surface, with little to no portion of the carbonized matrix directly stitched to the stent surface.

As the term is used herein, an "adhered drug layer" refers collectively to the post-GCIB irradiated layer comprised of at least one portion of non-carbonized deposited drug substance (s) and at least one carbonized matrix through which the deposited drug substance(s) is released at an expected rate. In embodiments described below, a drug delivery system comprised of multiple, adhered drug layers may subsequently be formed by repeatedly depositing additional layers of a selected drug substance onto a preceding adhered layer and irradiating the additional deposited drug layer with GCIB's. The selection of drug substance types, the method for depositing the drug (including sublimation) onto the medical device surface, and the control over GCIB dosing permits the precise formation of adhered drug layers such that a desired drug release rate, or elution profile, may be achieved in a multi-layered system. Subsequently adhered drug layers will have very few to no direct bonds between the carbonized matrix associated with the subsequent layer and the surface of the medical device. Rather, such layers will be adhered to preceding drug matrix layers. And in certain embodiments, the carbonized drug matrix of even the first layer will not be bonded, or stitched, to the stent surface.

In multi-layered embodiments of the invention, subsequent drug layers may be comprised of identical, similar or distinct drug substances. Additionally, identical, similar or different drug deposition techniques than those used to deposit preceding layers may be employed. Controlled variations in the GCIB characteristics and dosing delivered to different layers (and between spatially distinct regions of a single layer) may also be employed. Substantially similar GCIB doses delivered to substantially similar drug substances will result in similar drug elution profiles, while different doses can achieve distinct inter-layer elution profiles. Judicious selection of drug substance(s), and control over the deposition technique and GCIB dosing permits formation of a drug delivery system comprised of multiple, adhered drug layers each having similar or differing drug elution profiles which, in preferred embodiments of the invention, cooperate to achieve at least one overall drug elution profile. For example, the elution profiles of individual layers may be designed such that, as drug is diffused from the outermost adhered drug layer, it is replenished by drug(s) eluting from lower adhered layers.

A number of techniques may be employed to deposit the drug substance(s) onto the medical device surface, or one or more spatially distinct regions thereof. If the drug is to be deposited in liquid form, techniques such as dipping, spraying, vapor phase deposition, and ultrasonic atomization may be utilized. Alternatively, if the drug is in powder form, it may be electrostatically deposited onto the medical device surface or deposited by sublimation, and then GCIB irradiated in the same manner described above.

Any of the methods described may optionally include an irradiation step prior to drug deposition to obtain a smoother surface, which will help reduce non-uniform thickness in the adhered drug layer(s).

The application of drugs via GCIB surface modification such as described above will reduce complications, lead to genuine cost savings and an improvement in patient quality of life, and overcome prior problems of thrombosis and restenosis. Preferred therapeutic agents for delivery in the drug delivery systems of the present invention include anti-coagulants, antibiotics, immunosuppressant agents, vasodilators, anti-prolifics, anti-thrombotic substances, anti-platelet substances, cholesterol reducing agents, anti-tumor medications and combinations thereof.

BRIEF DESCRIPTION OF THE FIGURES

For a better understanding of the present invention, together with other and further objects thereof, reference is made to the accompanying drawings, wherein.

DETAILED DESCRIPTION OF PREFERRED EMBODIMENTS OF THE INVENTION

Figure 1:
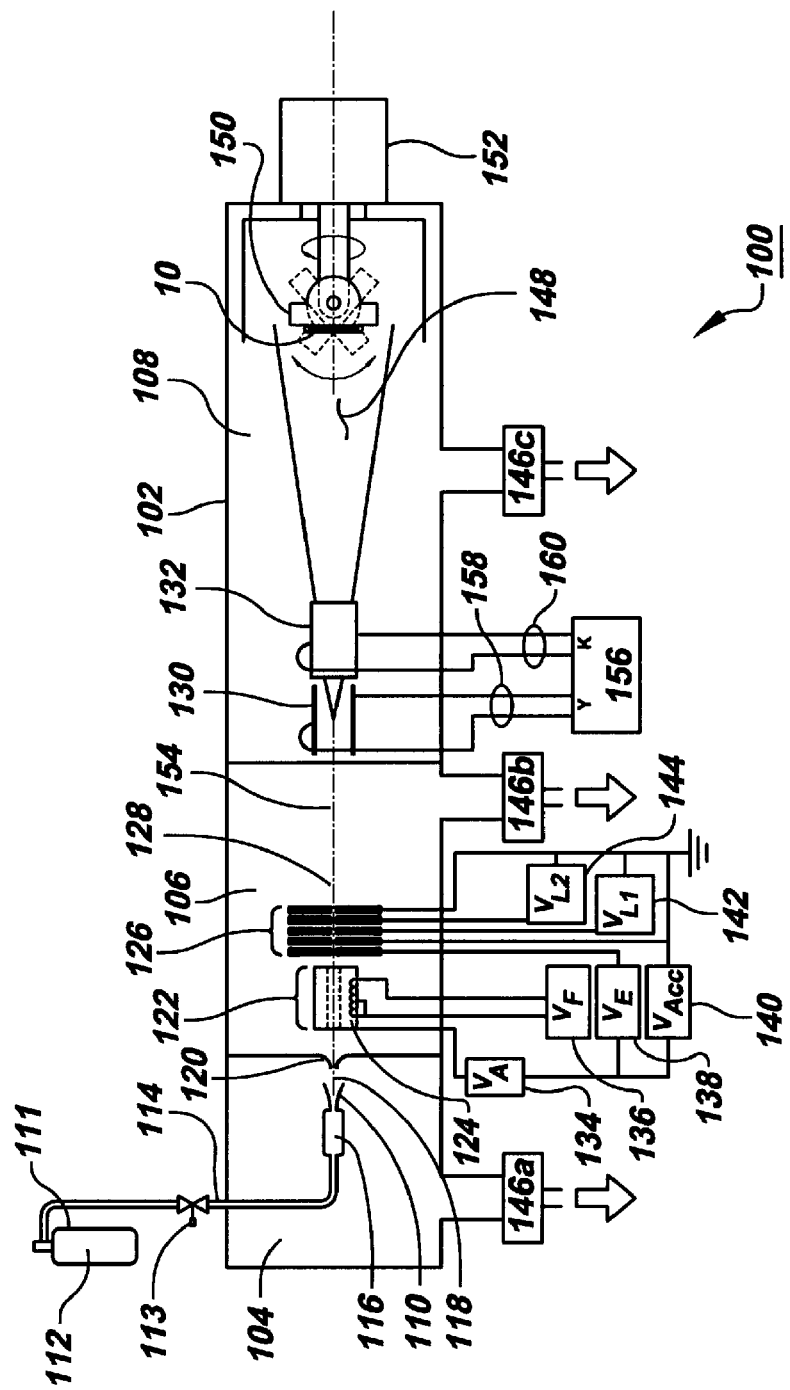
FIG. 1 is a schematic view of a gas cluster ion beam processing system of the present invention.

Beams of energetic ions, electrically charged atoms or molecules accelerated through high voltages under vacuum, are widely utilized to form semiconductor device junctions, to smooth surfaces by sputtering, and to enhance the properties of thin films. In the present invention, these same beams of energetic ions are utilized for the applying and adhering drugs to a surface of a medical device, such as a coronary stent, thereby converting the surface into a drug delivery system.

In the preferred embodiment of the present invention, gas cluster ion beam GCIB processing is utilized. Gas cluster ions are formed from large numbers of weakly bound atoms or molecules sharing common electrical charges and accelerated together through high voltages to have high total energies. Cluster ions disintegrate upon impact and the total energy of the cluster is shared among the constituent atoms. Because of this energy sharing, the atoms are individually much less energetic than the case of conventional ions or ions not clustered together and, as a result, the atoms penetrate to much shorter depths. Surface sputtering effects are orders of magnitude stronger than corresponding effects produced by conventional ions, thereby making important microscale surface effects possible that are not possible in any other way.

The concept of GCIB processing has only emerged over the past decade. Using a GCIB for dry etching, cleaning, and smoothing of materials is known in the art and has been described, for example, by Deguchi, et al. in U.S. Pat. No. 5,814,194, "Substrate Surface Treatment Method", 1998. Because ionized clusters containing on the order of thousands of gas atoms or molecules may be formed and accelerated to modest energies on the order of a few thousands of electron volts, individual atoms or molecules in the clusters may each only have an average energy on the order of a few electron volts. It is known from the teachings of Yamada in, for example, U.S. Pat. No. 5,459,326, that such individual atoms are not energetic enough to significantly penetrate a surface to cause the residual sub-surface damage typically associated with plasma polishing. Nevertheless, the clusters themselves are sufficiently energetic (some thousands of electron volts) to effectively etch, smooth, or clean hard surfaces.

Because the energies of individual atoms within a gas cluster ion are very small, typically a few eV, the atoms penetrate through only a few atomic layers, at most, of a target surface during impact. This shallow penetration of the impacting atoms means all of the energy carried by the entire cluster ion is consequently dissipated in an extremely small volume in the top surface layer during a period on the order of $10^{-12}$ seconds (i.e. one picosecond). This is different from the case of ion implantation which is normally done with conventional monomer ions and where the intent is to penetrate into the material, sometimes penetrating several thousand angstroms, to produce changes in the surface properties of the material. Because of the high total energy of the cluster ion and extremely small interaction volume, the deposited energy density at the impact site is far greater than in the case of bombardment by conventional monomer ions.

Reference is now made to FIG. 1 of the drawings which shows the GCIB processor 100 of this invention utilized for applying or adhering drugs to the surface of a medical device such as, for example, coronary stent 10. Although not limited to the specific components described herein, the processor 100 is made up of a vacuum vessel 102 which is divided into three communicating chambers, a source chamber 104, an ionization/acceleration chamber 106, and a processing chamber 108 which includes therein a uniquely designed workpiece holder 150 capable of positioning the medical device for uniform GCIB bombardment and drug application by a gas cluster ion beam.

During the drug application method of this invention, the three chambers are evacuated to suitable operating pressures by vacuum pumping systems 146a, 146b, and 146c, respectively. A condensable source gas 112 (for example argon or $N_2$) stored in a cylinder 111 is admitted under pressure through gas metering valve 113 and gas feed tube 114 into stagnation chamber 116 and is ejected into the substantially lower pressure vacuum through a properly shaped nozzle 110, resulting in a supersonic gas jet 118. Cooling, which results from the expansion in the jet, causes a portion of the gas jet 118 to condense into clusters, each consisting of from several to several thousand weakly bound atoms or molecules. A gas skimmer aperture 120 partially separates the gas molecules that have not condensed into a cluster jet from the cluster jet so as to minimize pressure in the downstream regions where such higher pressures would be detrimental (e.g., ionizer 122, high voltage electrodes 126, and process chamber 108). Suitable condensable source gases 112 include, but are not necessarily limited to, argon, nitrogen, carbon dioxide, oxygen.

After the supersonic gas jet 118 containing gas clusters has been formed, the clusters are ionized in an ionizer 122. The ionizer 122 is typically an electron impact ionizer that produces thermoelectrons from one or more incandescent filaments 124 and accelerates and directs the electrons causing them to collide with the gas clusters in the gas jet 118, where the jet passes through the ionizer 122. The electron impact ejects electrons from the clusters, causing a portion the clusters to become positively ionized. A set of suitably biased high voltage electrodes 126 extracts the cluster ions from the ionizer 122, forming a beam, then accelerates the cluster ions to a desired energy (typically from 1 keV to several tens of keV) and focuses them to form a GCIB 128 having an initial trajectory 154. Filament power supply 136 provides voltage $V_F$ to heat the ionizer filament 124. Anode power supply 134 provides voltage $V_A$ to accelerate thermoelectrons emitted from filament 124 to cause them to bombard the cluster containing gas jet 118 to produce ions. Extraction power supply 138 provides voltage $V_E$ to bias a high voltage electrode to extract ions from the ionizing region of ionizer 122 and to form a GCIB 128. Accelerator power supply 140 provides voltage $V_{Acc}$ to bias a high voltage electrode with respect to the ionizer 122 so as to result in a total GCIB acceleration energy equal to $V_{Acc}$ electron volts (eV). One or more lens power supplies (142 and 144, for example) may be provided to bias high voltage electrodes with potentials ($V_{L1}$ and $V_{L2}$ for example) to focus the GCIB 128.

A medical device, such as coronary stent 10, to be processed by the GCIB processor 100 is held on a workpiece holder 150, and disposed in the path of the GCIB 128 for irradiation. The present invention may be utilized with medical devices composed of a variety of materials, such as metal, polyethylene, ceramic, or combinations thereof. In order for the stent to be uniformly processed using GCIB, the workpiece holder 150 is designed in a manner set forth below to manipulate the stent 10 in a specific way.

Figure 2:
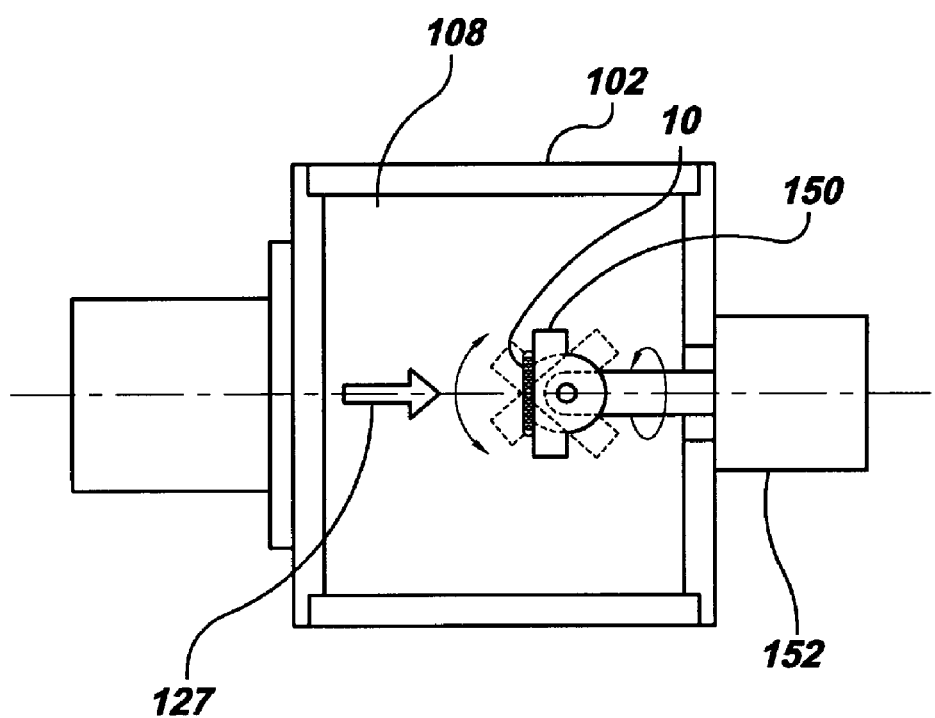
FIG. 2 is an exploded view of a portion of the gas cluster ion beam processing system showing the workpiece holder.

Referring now to FIG. 2 of the drawings, medical device surfaces that are non-planar, such as those of stents, must remain oriented within a specific angle tolerance with respect to the normal beam incidence to obtain paramount effect to the stent surfaces utilizing GCIB. This requires a fixture or workpiece holder 150 with the ability to be fully articulated to orient all non-planar surfaces of stent 10 to be modified within that specific angle tolerance at a constant exposure level for process optimization and uniformity. Any stent 10 containing surfaces that would be exposed to the process beam at angles of greater than +/−15 degrees from normal incidence may require manipulation. More specifically, when applying GCIB to a coronary stent 10, the workpiece holder 150 is rotated and articulated by a mechanism 152 located at the end of the GCIB processor 100. The articulation/rotation mechanism 152 preferably permits 360 degrees of device rotation about longitudinal axis 154 and sufficient device articulation about an axis 156 perpendicular to axis 154 to maintain the stent's surface to within +/−15 degrees from normal beam incidence.

Under certain conditions, depending upon the size of the coronary stent 10, a scanning system may be desirable to produce uniform smoothness. Although not necessary for GCIB processing, two pairs of orthogonally oriented electrostatic scan plates 130 and 132 may be utilized to produce a raster or other scanning pattern over an extended processing area. When such beam scanning is performed, a scan generator 156 provides X-axis and Y-axis scanning signal voltages to the pairs of scan plates 130 and 132 through lead pairs 158 and 160 respectively. The scanning signal voltages are commonly triangular waves of different frequencies that cause the GCIB 128 to be converted into a scanned GCIB 148, which scans the entire surface of the stent 10. Additional means for orienting, articulating and/or rotating devices such as stents and orthopedic products are disclosed in U.S. Pat. No. 6,491,800 to Kirkpatrick, et al., U.S. Pat. No. 6,676,989 to Kirkpatrick, et al., and U.S. Pat. No. 6,863,786 to Blinn, et al., the contents of each which are hereby incorporated by reference.

When beam scanning over an extended region is not desired, processing is generally confined to a region that is defined by the diameter of the beam. The diameter of the beam at the stent's surface can be set by selecting the voltages ($V_{L1}$ and/or $V_{L2}$) of one or more lens power supplies (142 and 144 shown for example) to provide the desired beam diameter at the workpiece.

In one embodiment of the present invention, the surface of the medical device is irradiated with a GCIB prior to the deposition of any drug on the surface thereof. This will remove any contaminants and oxide layers from the stent surface rendering the surface electrically active and capable of attracting and bonding drug molecules that are then introduced to the surface. One or more types of drugs are deposited upon surface through vapor phase deposition or by introducing a liquid form of the drug onto the surface. In some instances, the liquid form of the drug is in solution with a volatile solvent thereby requiring the solvent to be evaporated. As the formed mechanical bonds are broken over time, the drug is slowly released to the site of device implantation.

Studies have suggested that a wide variety of drugs may be useful at the site of contact between the medical device and the in vivo environment. For example, drugs such as anti-coagulants, anti-prolifics, antibiotics, immune-supressing agents, vasodilators, anti-thrombotic substances, anti-platelet substances, and cholesterol reducing agents may reduce instances of restenosis when diffused into the blood vessel wall after insertion of the stent.

In other embodiments of the present invention, GCIB processing is utilized to impact a deposited drug layer (and the surface of the medical device if the deposited drug layer is thin enough to permit gas clusters penetration to the surface) with energetic clusters thus implanting and forming a mechanical bond between the surface and the deposited drug molecules; or to implant the drug molecules of the electrostatically coated or sublimated medicine in powder form to the stent surface in the same manner described above. The impact energy of the gas clusters causes a portion of the deposited drug molecules to form a carbonized drug matrix. As the carbon matrix is formed, the remaining (non-carbonized) drug molecules become embedded within the interstices of the matrix, and/or are encapsulated between the carbon matrix and the medical device surface. Over time, these drug molecules diffuse through the matrix and are released at the contact site between the stent and the blood vessel wall thereby continuously providing medication to the site.

Figure 3:
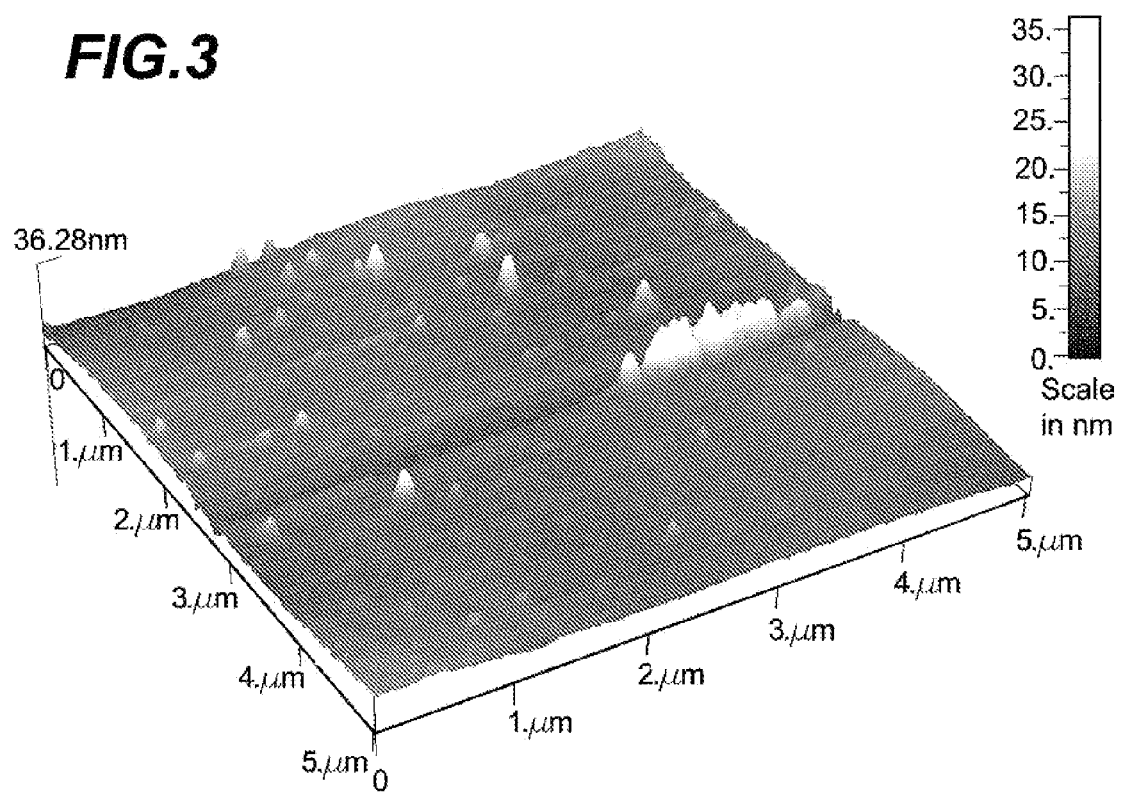
FIG. 3 is an atomic force microscope image showing the surface of a coronary stent before GCIB processing.
Figure 4:
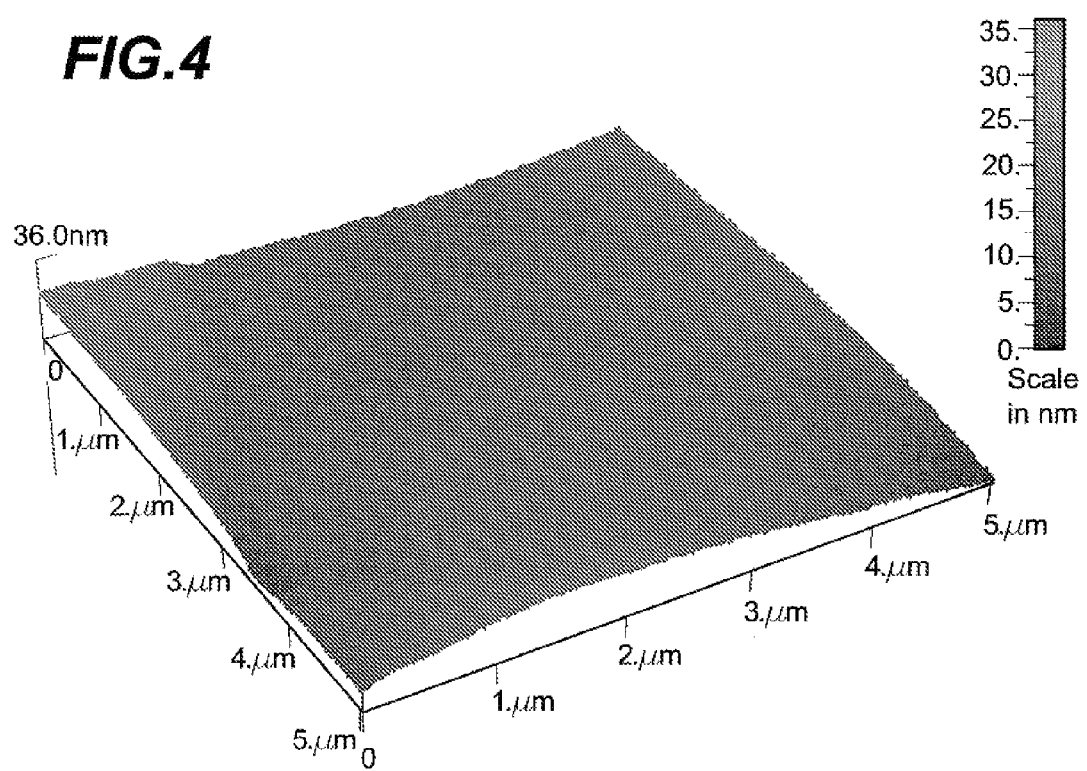
FIG. 4 is an atomic force microscope image showing the surface of a coronary stent after GCIB processing.

As the atomic force microscope (AFM) images shown in FIGS. 3 and 4 demonstrate, it is possible to dramatically affect the medical device surface utilizing one embodiment of the present invention. FIG. 3 shows a stent surface before GCIB treatment with gross surface micro-roughness on a strut edge. The surface roughness measured an $R_a$ of 113 angstroms and an $R_{RMS}$ of 148 angstroms. These irregularities highlight the surface condition at the cellular level where thrombosis begins. FIG. 4 shows the stent surface after GCIB processing where the surface micro-roughness has been eliminated without any measurable physical or structural change to the integrity of the stent itself. The post-GCIB surface roughness measured an $R_a$ of 19 angstroms and an $R_{RMS}$ of 25 angstroms. In this manner, GCIB processing also provides the added benefit of smoothing the surface of the medical device while applying/adhering the drug to the surface. Non-smooth surfaces may snare fibrinogen, platelets, and other matter further promoting stenosis.

Figure 5A:
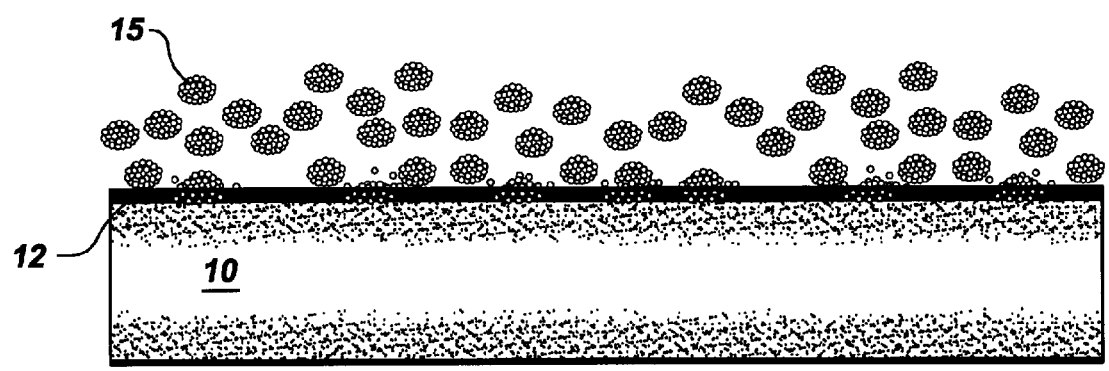
FIGS. 5A-5H are illustrations of a surface region of a medical device at various stages of drug delivery system formation in accordance with an embodiment of the present invention.

With reference to FIGS. 5A-5F, a method of producing a drug delivery system will now be described. FIG. 5A illustrates a surface region 12 of a medical device such as, for example, stent 10, that has been positioned in a vacuum chamber such that it can be irradiated with gas clusters 15 of a GCIB, as would occur in an optional smoothing process step. FIG. 6A illustrates an exemplary drug delivery structure in accordance with an embodiment of the present invention. Note that the drug delivery structure may cover all or less than the entirety of the exterior surface of stent 10. In the latter case, surface region 12 represents but one of a plurality of spatially distinct surface regions 12-14 of stent 10 upon which the drug delivery system is formed. Each of the distinct surface regions 12-14 may elute the same or similar type of drug, or completely distinct types of drugs. For ease in understanding, the description that follows focuses on the formation of the drug delivery structure at surface region 12 only.

Figure 5B:
Figure 5C:
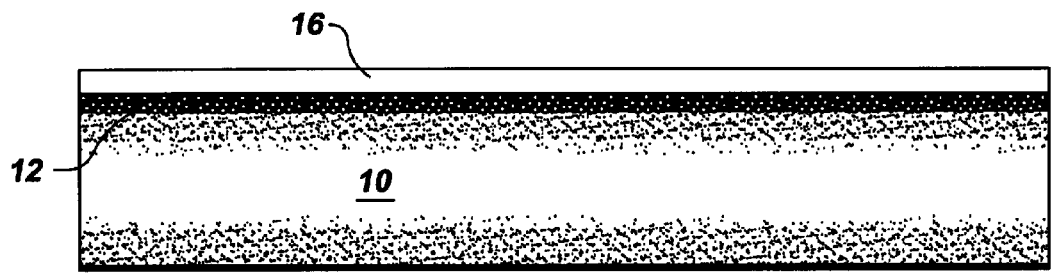
Figure 6A:
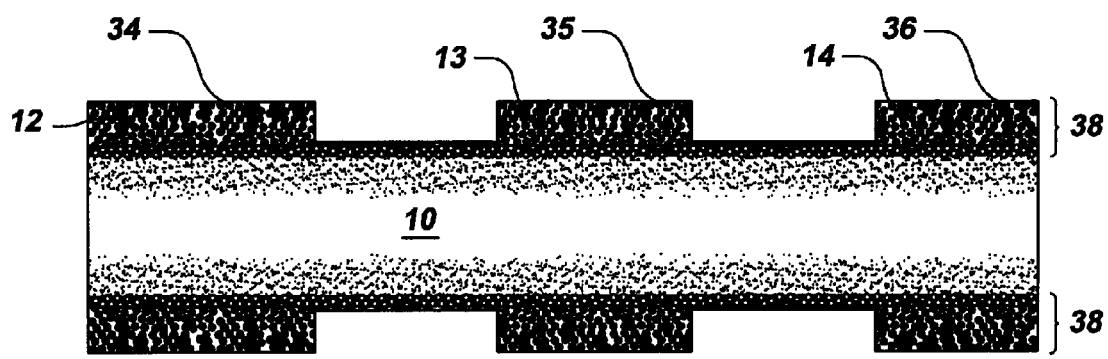
FIGS. 6A-6B are illustrations of alternative drug delivery structure embodiments in accordance with the present invention.

FIG. 5B illustrates surface region 12 as being relatively smooth, following an optional surface preparation step through GCIB irradiation. As described above, such processing removes contaminants and electrically activates the surface region 12. FIG. 5C shows a drug layer 16, which may be deposited by any of the techniques described above, and which preferably has been deposited to have a substantially uniform thickness in the vicinity of region 12. A "deposited drug layer" is used herein to refer to a contiguous drug layer deposited over the entirety of the surface of the medical device, such as deposited drug layer 16, or alternatively may be used in a collective sense to refer to numerous spatially distinct deposits of the same or different therapeutic agents on the surface 12. In either case, the deposited drug layer is GCIB irradiated to form an adhered drug layer on the device surface from which a portion of the deposited agent will be released over time to a patient's tissue adjacent the medical device.

Figure 5D:
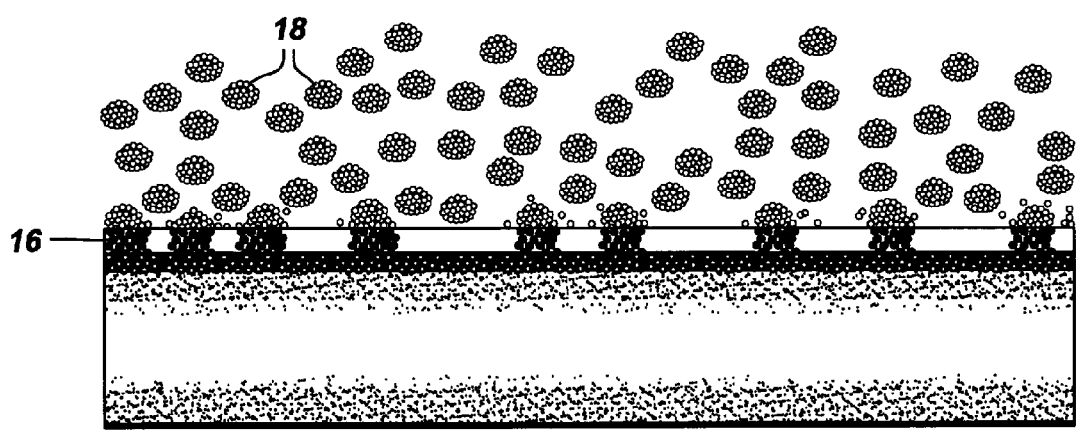
Figure 5E:
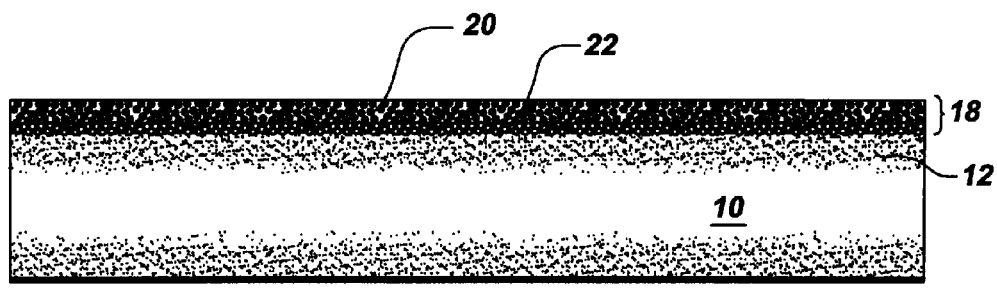

FIG. 5D illustrates the step of irradiating the first deposited drug layer 16 with GCIB gas clusters 18. This results in the formation of a first adhered drug layer 18, which is comprised of two primary components, such as shown in FIG. 5E. First adhered drug layer 18, and subsequently formed adhered drug layers, each include a carbonized drug matrix 20 having a plurality of interstices 22 in which will be disposed the remainder of the deposited drug that was not carbonized by the GCIB. Drug layer 18 is adhered to the surface region 12, and a portion of the non-carbonized drug will be released at an expected rate (characterized as an elution profile) from the adhered drug layer 18 by diffusion through the interstices 22 of the carbonized drug matrix 20. A number of the interstices 22 are interconnected, and a portion of the interstices are open at each surface of the drug matrix 20 so as to permit non-carbonized drug to eventually elute from a substantial number of the interstices 22 of the drug matrix 20.

Figure 5F:
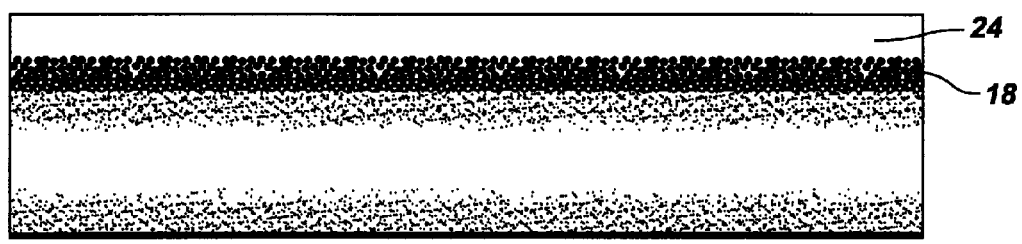
Figure 5G:
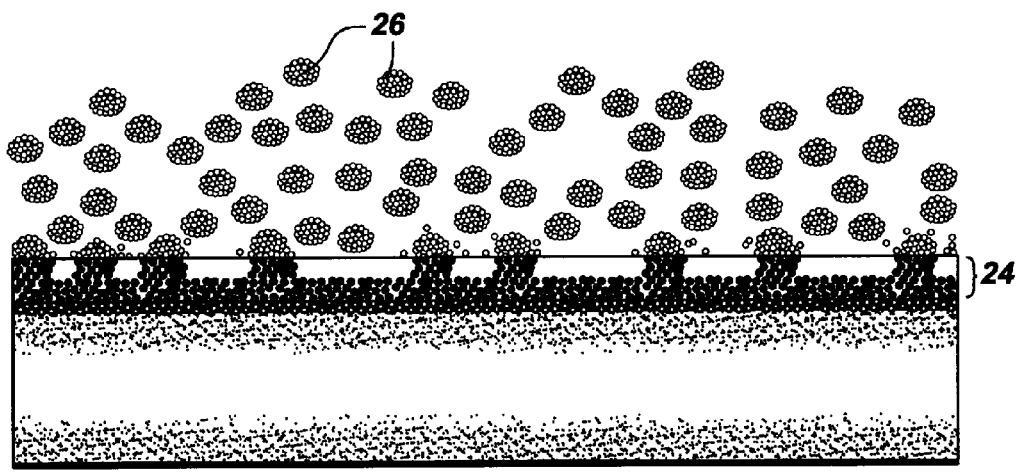
Figure 5H:
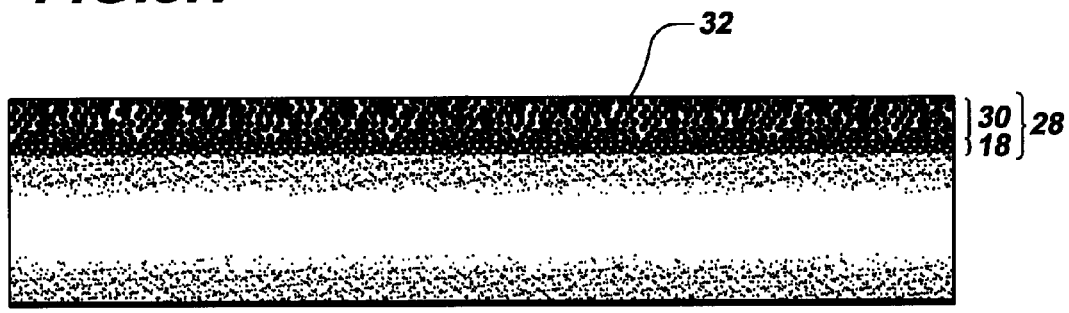

FIGS. 5F-5H illustrate how the drug deposition and GCIB irradiation process steps may be repeated, generally, to achieve multi-layered drug delivery structures having variable and extremely accurate drug loading. More particularly, FIG. 5F illustrates a second drug layer 24 deposited upon the first adhered drug layer 18 using the same or an alternative deposition process. The second drug layer 24 is then irradiated (FIG. 5G) with GCIB gas clusters 26 delivering substantially similar dosing or different, depending upon desired elution profile. Similar GCIB irradiation doses delivered to substantially similar or identical therapeutic agents will result in substantially similar elution profiles between or among adhered layers. FIG. 5H illustrates a drug delivery system comprised of an adhered drug layer 28 that is further comprised of the first adhered drug layer 18 and a second adhered drug layer 30. As many repetitions of the drug deposition and GCIB irradiation steps as needed to attain an overall elution profile, or profiles (if multiple therapeutic agents are utilized), may be performed. In one preferred embodiment, the first adhered drug layer 18 and second adhered drug layer 30 are similarly formed to have similar elution profiles, such that, as drug is released from the interstices 32 of layer 30, drug eluting from layer 18 into layer 30 replenishes the released drug. The adhered drug layers 18, 30 are not necessarily, however, comprised of the same drug substance(s).

Several alternative drug delivery systems in accordance with the present invention will now be described, with reference to FIGS. 6A-6B.

As noted above, multiple factors, including the thickness of the deposited drug layer, will determine whether GCIB gas clusters will penetrate a deposited drug layer so as to reach the surface onto which a new drug layer is to be adhered. FIG. 6A (and FIG. 5E) illustrates a drug delivery system 38 that is further comprised of spatially distinct adhered drug structures 34-36 formed when GCIB gas clusters penetrate a thinly deposited drug layer (e.g., on the order of several to tens of Angstroms, or greater.) Note that some portion of the adhered drug structures 34-36 are bonded (or stitched) to associated, spatially distinct surface regions 12-14. Formation of each of the adhered drug structures 34-36 may be accomplished nearly simultaneously or in separate processing routines. The therapeutic agent to be released from each of the adhered drug structures 34-36 is deposited at the associated spatially distinct surface region 12-14 and then GCIB irradiated. Again, the drug deposited at each surface region 12-14 is not necessarily the same. Forming adhered drug structures on less than the entire surface of the medical device has the benefit of cost savings when an expensive drug is to be used. Also, certain drugs may only need to be delivered at particular locations, such as at a site of significant tissue interaction with an implanted medical device.

Figure 6B:
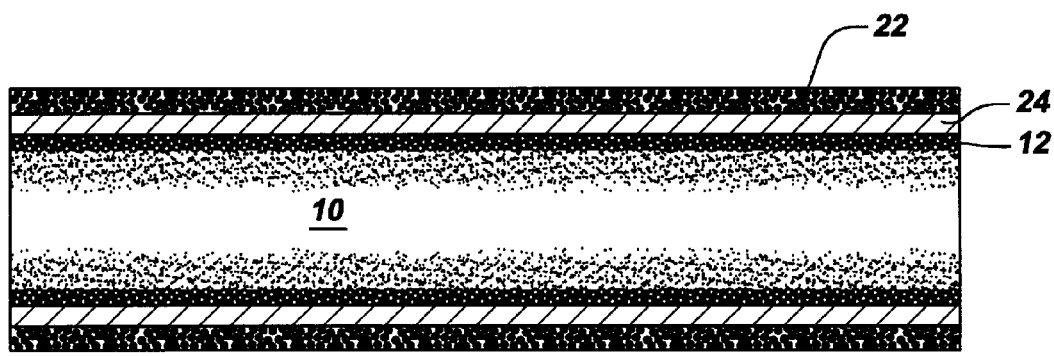

FIG. 6B illustrates an alternative embodiment of a drug delivery system, such as may be formed when the GCIB does not penetrate the thickness of a drug layer deposited on the surface region 12 of the medical device 10. In such embodiments, a carbonized drug matrix 22 is still formed having interstices within which some portion of non-carbonized drug is disposed, and from which non-carbonized drug is released, however the drug matrix 22 does not extend to the surface 12 of the medical device 10. Rather, the carbonized matrix 22 encapsulates the remainder of deposited drug 24 that was not carbonized by the GCIB (and not captured in the interstices), between the drug matrix 22 and the surface 12 of the device 10. As noted above, the expression "adhered drug layer" as used herein refers collectively to the carbonized matrix 22, and the non-carbonized portions of the deposited drug, whether disposed in the interstices or encapsulated by the drug matrix 22 and the device surface.

Figure 7A:
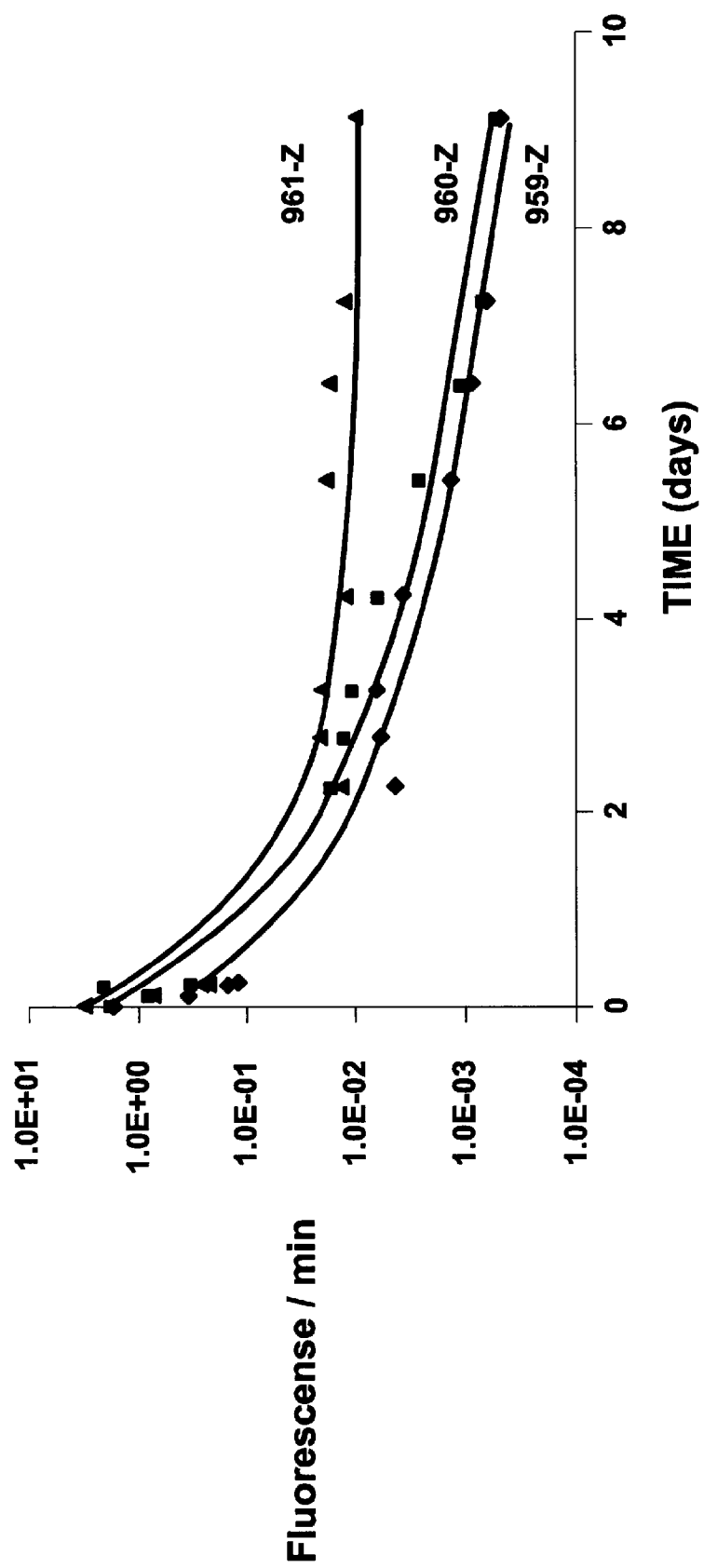
FIG. 7A is a graph showing the release rate of fluorescence over time.
Figure 7B:
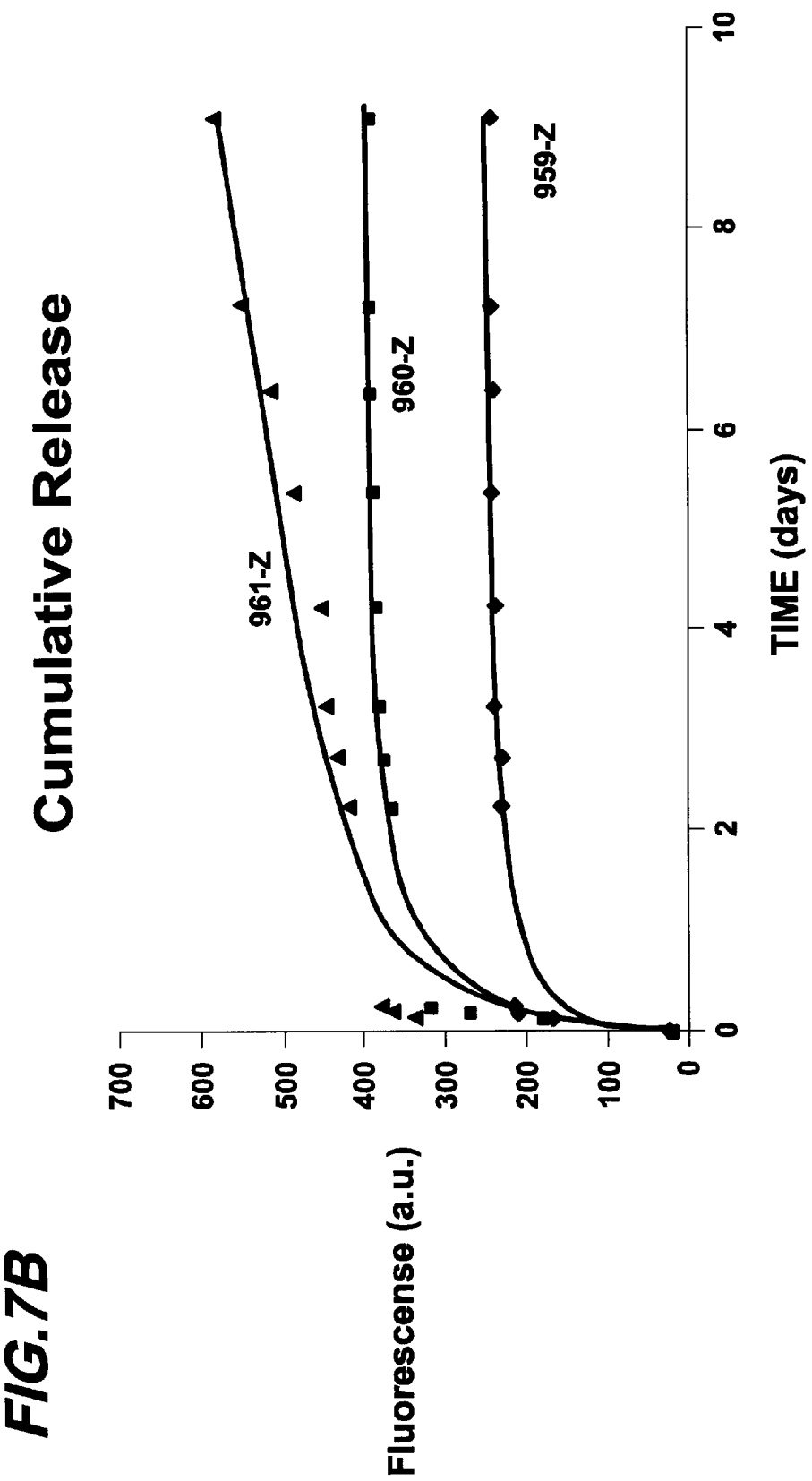
FIG. 7B is a graph showing the cumulative release rate of fluorescence over time.

Now turning to FIGS. 7A and 7B, elution rates for a substance adhered to a surface of a coronary stent using GCIB processing in accordance with the present invention is shown. To demonstrate the release rate of a molecule adhered to the surface in accordance with the present invention, the surface was irradiated and a flourescent organic dye was vapor deposited onto the freshly irradiated surface while the surface remained in the vacuum chamber. The dye elution rate was measured by observing the flourescence of the elute as a function of time. In FIG. 7A, the release rate is shown over time. In FIG. 7B, the cumulative release rate is shown over time.

Figure 8:
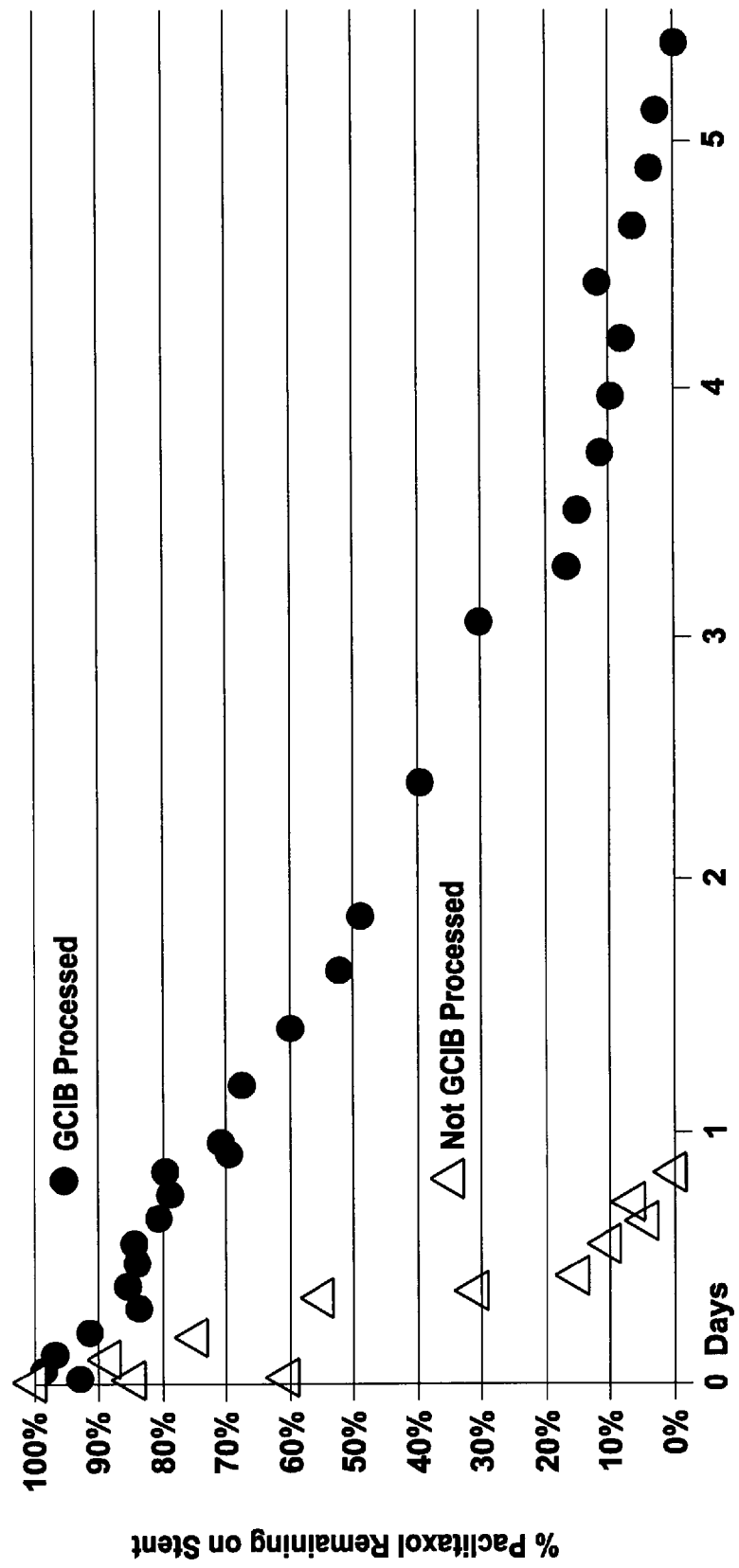
FIG. 8 is a graph showing comparative drug elution rate test results for a conventional drug-coated stent and a stent processed in accordance with the present invention.

FIG. 8 illustrates results of comparative elution rate testing performed on a conventional drug-coated stent and a stent upon which an exemplary drug delivery system has been firmed utilizing GCIB irradiation in accordance with the present invention. Paclitaxol was selected as the test drug, which in the case of the non-GCIB processed stent was deposited, and for the GCIB processed stent was deposited by ultrasonic atomization prior to being irradiated with an Argon GCIB while rotating the stent between 3-5 RPM. The Paclitaxol was allowed to elute from the respective stents over time into a 4% Bovine Serum Albumin/Phosphate Buffered Saline solution, and the drug remaining on the stents was measured. As shown, significantly more drug remained loaded on the drug-adhered stent for a longer period of time that the conventional drug coated stent Although the invention has been described with respect to various embodiments, it should be realized this invention is also capable of a wide variety of further and other embodiments within the spirit and scope of the appended claims.

It is claimed:

1. Method of producing a drug delivery system, comprising the steps of:
    depositing a drug substance onto at least one surface region of a medical device so as to form a first deposited drug layer;
    forming a first gas cluster ion beam in a vacuum chamber;
    positioning the at least one surface region of the medical device in the vacuum chamber for irradiation by the first gas cluster ion beam; and
    irradiating the first deposited drug layer with the first gas cluster ion beam so as to adhere a drug layer to the at least one surface region of the medical device such that a portion of the deposited drug substance is permitted to be released from the first adhered drug layer at an expected rate.

2. The method of claim 1, wherein some portion of gas clusters comprising the gas cluster ion beam penetrate the first deposited drug layer and irradiate the surface of the medical device.

3. The method of claim 1, wherein the adhered drug layer comprises at least one carbonized matrix formed of a portion the first deposited drug layer and including a plurality of interstices within which is disposed a non-carbonized portion of the first deposited drug layer, a plurality of the interstices being open at a surface of the carbonized matrix so as to permit the non-carbonized portion of the first deposited drug layer to be released at the expected rate.

4. The method of claim 3, wherein the adhered drug layer further comprises another non-carbonized portion of the first deposited drug layer that is encapsulated between the carbonized matrix and the at least one surface region of the medical device.

5. The method of claim 1, further comprising the steps, repeated until an desired number of additional adhered drug layers are formed, of:
   depositing an additional drug layer onto the most recently adhered drug layer; and
   irradiating the additional drug layer with an additional gas cluster ion beam so as to adhere an additional drug layer onto the most recently adhered drug layer such that a portion of the additional deposited drug substance is permitted to be released from the additional adhered drug layer at an expected rate.

6. The method of claim 5, wherein the drug substances respectively comprising the first deposited drug layer and the additional deposited drug layer are comprised of the same drug substance type.

7. The method of claim 5, wherein the first gas cluster beam and the additional gas cluster ion beam deliver substantially similar irradiation doses resulting in substantially similar drug elution profiles between the first adhered drug layer and the additional adhered drug layer(s).

8. The method of claim 5, wherein the first gas cluster beam and the additional gas cluster ion beam deliver different irradiation doses resulting in different drug elution profiles between the first adhered drug layer and the additional adhered drug layer(s).

9. The method of claim 1, wherein:
   the at least one surface region comprises a plurality of spatially distinct regions of the surface of the medical device;
   the first drug layer is comprised of a corresponding plurality of drug substance portions; and
   the depositing step comprises depositing each portion of the drug substance onto a corresponding one of the plurality of spatially distinct regions.

10. The method of claim 1, further comprising gas cluster ion beam irradiating the at least one surface region of the medical device prior to depositing the drug substance so as to smoothen the at least one surface region.

11. The method of claim 1, wherein the depositing step comprises vapor phase depositing the drug substance onto the at least one surface region.

12. The method of claim 1, wherein the depositing step comprises ultrasonically atomizing the drug substance onto the at least one surface region.

13. The method of claim 1, wherein the depositing step comprises electrostatically coating the at least one surface region with the drug substance in powder form.

14. The method of claim 1, wherein the depositing step comprises sublimating the at least one surface region with the drug substance.

15. The method of claim 1, wherein the at least one surface region comprises the entirety of the surface of the medical device.

16. The method of claim 1, wherein the medical device surface is comprised of at least one material selected from polymers, metals and ceramics.

17. The method of claim 3, wherein two or more of the interstices are interconnected.

18. The method of claim 1, further comprising the step of selecting the drug substance from the group consisting of anti-coagulants, antibiotics, anti-tumor substances, immune-suppressing agents, vasodilators, anti-prolifics, anti-thrombotic substances, anti-platelet substances, cholesterol reducing agents and combinations thereof.

19. The method of claim 1, wherein the irradiating step further comprises scanning the gas cluster ion beam over an extended processing area of the at least one surface region.

20. The method of claim 1, wherein the irradiating step further comprises maintaining an orientation within a specific angle tolerance between the gas cluster ion beam and the at least one surface region being irradiated.

\* \* \* \* \*

UNITED STATES PATENT AND TRADEMARK OFFICE
CERTIFICATE OF CORRECTION

| | | |
|---|---|---|
| PATENT NO. | : 8,187,662 B2 | Page 1 of 1 |
| APPLICATION NO. | : 12/643047 | |
| DATED | : May 29, 2012 | |
| INVENTOR(S) | : Stephen M. Blinn et al. | |

It is certified that error appears in the above-identified patent and that said Letters Patent is hereby corrected as shown below:

In column 10, line 59 (claim 3), "a portion" should read --a portion of--

Signed and Sealed this
Tenth Day of July, 2012

David J. Kappos
*Director of the United States Patent and Trademark Office*